United States Patent [19]

McClarron et al.

[11] Patent Number: 5,466,876
[45] Date of Patent: Nov. 14, 1995

[54] PROCESS FOR THE REMOVAL OF CORROSION METAL CONTAMINANTS FROM LIQUID COMPOSITIONS

[75] Inventors: Andrew R. McClarron, Beverley; Stephen J. Smith, Hull; Derrick J. Watson, Hornsea; Bruce L. Williams, Elloughton, all of United Kingdom; Euan S. Ross, Grand Bahama, Bahamas

[73] Assignee: BP Chemicals Limited, London, England

[21] Appl. No.: 206,072

[22] Filed: Mar. 4, 1994

[30] Foreign Application Priority Data

Mar. 22, 1993 [GB] United Kingdom ............... 9305902

[51] Int. Cl.$^6$ .................... C07C 51/12; C07C 53/08; B01J 31/30
[52] U.S. Cl. .................... 562/608; 560/248; 210/665; 210/679; 210/683
[58] Field of Search .................... 562/608; 560/248; 210/665, 679, 683

[56] References Cited

U.S. PATENT DOCUMENTS

| | | |
|---|---|---|
| 4,007,130 | 2/1977 | Leach et al. . |
| 4,113,754 | 9/1978 | Kummer et al. . |
| 4,303,704 | 12/1981 | Courduvelis et al. . |
| 4,365,099 | 12/1982 | Faler et al. . |
| 4,374,070 | 2/1983 | Larkins et al. . |
| 4,628,041 | 12/1986 | Smith et al. . |
| 4,894,477 | 1/1990 | Scates et al. . |
| 5,124,290 | 6/1992 | Erpenbach et al. . |
| 5,220,058 | 6/1993 | Fish et al. ............... 562/608 |
| 5,344,976 | 9/1993 | Jones et al. ............... 562/608 |
| 5,367,104 | 3/1994 | Leupold ................... 570/211 |

FOREIGN PATENT DOCUMENTS

| | | |
|---|---|---|
| 0087870 | 9/1983 | European Pat. Off. . |
| 0144936 | 6/1985 | European Pat. Off. . |
| 1144935 | 6/1985 | European Pat. Off. . |
| 0161874 | 11/1985 | European Pat. Off. . |
| 0255389 | 2/1988 | European Pat. Off. . |
| 0265140 | 4/1988 | European Pat. Off. . |
| 0314352 | 5/1989 | European Pat. Off. . |
| 0364824 | 4/1990 | European Pat. Off. . |
| 0384652 | 8/1990 | European Pat. Off. . |
| 0479463 | 4/1992 | European Pat. Off. . |
| 0538040 | 4/1993 | European Pat. Off. . |
| 0584964 | 3/1994 | European Pat. Off. . |
| 211352 | 7/1984 | Germany . |
| 422439 | 1/1992 | Japan . |
| 1233121 | 5/1971 | United Kingdom . |
| 1476815 | 6/1977 | United Kingdom . |
| 2146637A | 4/1985 | United Kingdom . |
| 8702273 | 4/1987 | WIPO . |

OTHER PUBLICATIONS

Chemical Abstracts, vol. 98, p. 214: 183072.2, 1983.
Analytical Chemistry, vol. 46, No. 6, May 1974, "Concentration of Heavy Metals by Complexation on Dithiocarbamate Resins", J. F. Dingman, Jr. et al.
Analyst, May 1980, vol. 105, pp. 491–496, "Application of Chelating Resin to the Determination of Trace Amounts of Mercury in Natural Waters", E. Yamagami et al.
Analytica Chemica Acta, 115 (1980) 103–110, "Determination of Very Low Levels Absorption Spectrometry After Preconcentration on a Chelating Resin", K. Minagawa et al.
Analytica Chimica Acta, 113 (1980) 139–147, "Preparation of Dithiocarbamate–cellulose Derivatives and Their Absorption Properties for Trace Elements", S. Imai et al.
Ion Exchange: Science and Technology, 1986, "Applications of Ion Exchange in Hydrometallurgy", A. E. Rodrigues.
Ion Exchange Technology, 1984, pp. 724–735, D. Naden and M. Streat Editors, Ellis Horwood Ltd. publ., Society of Chemical Industry (1984) "A Comparative Study of Some Chelating Ion Exchange Resins for Applications in Hydrometallurgy", J. Melling and D. W. West.
Abstract of Japanese Patent Application No. 53–101,310, published Sep. 4, 1978.
Abstract of Japanese Patent Application No. 4–055,312, published Feb. 24, 1992.
Abstract of Japanese Patent Application No. 2–187,143, published Jul. 23, 1990.
Abstract of Japanese Patent Application No. 1–230,799, published Sep. 14, 1989.
Abstract of Japanese Patent Application No. 63–125,504 published May 28, 1988.
Abstract of Japanese Patent Application No. 52–086,975 published Jul. 20, 1977.
Abstract of Netherlands Patent Application No. NL 7 409 303, published Jul. 10, 1974.
Deloxan—Metallabsorber Technische Daten from Degussa, Nov., 1990.

*Primary Examiner*—Arthur C. Prescott
*Attorney, Agent, or Firm*—Brooks Haidt Haffner & Delahunty

[57] ABSTRACT

Corrosion metal contaminants are removed from a liquid composition comprising a carboxylic acid and/or an anhydride thereof, a rhodium carbonylation catalyst, and a carbonylation catalyst co-promoter by using a chelating resin selective for the removal of corrosion metals rather than carbonylation catalyst and co-promoter.

20 Claims, 1 Drawing Sheet

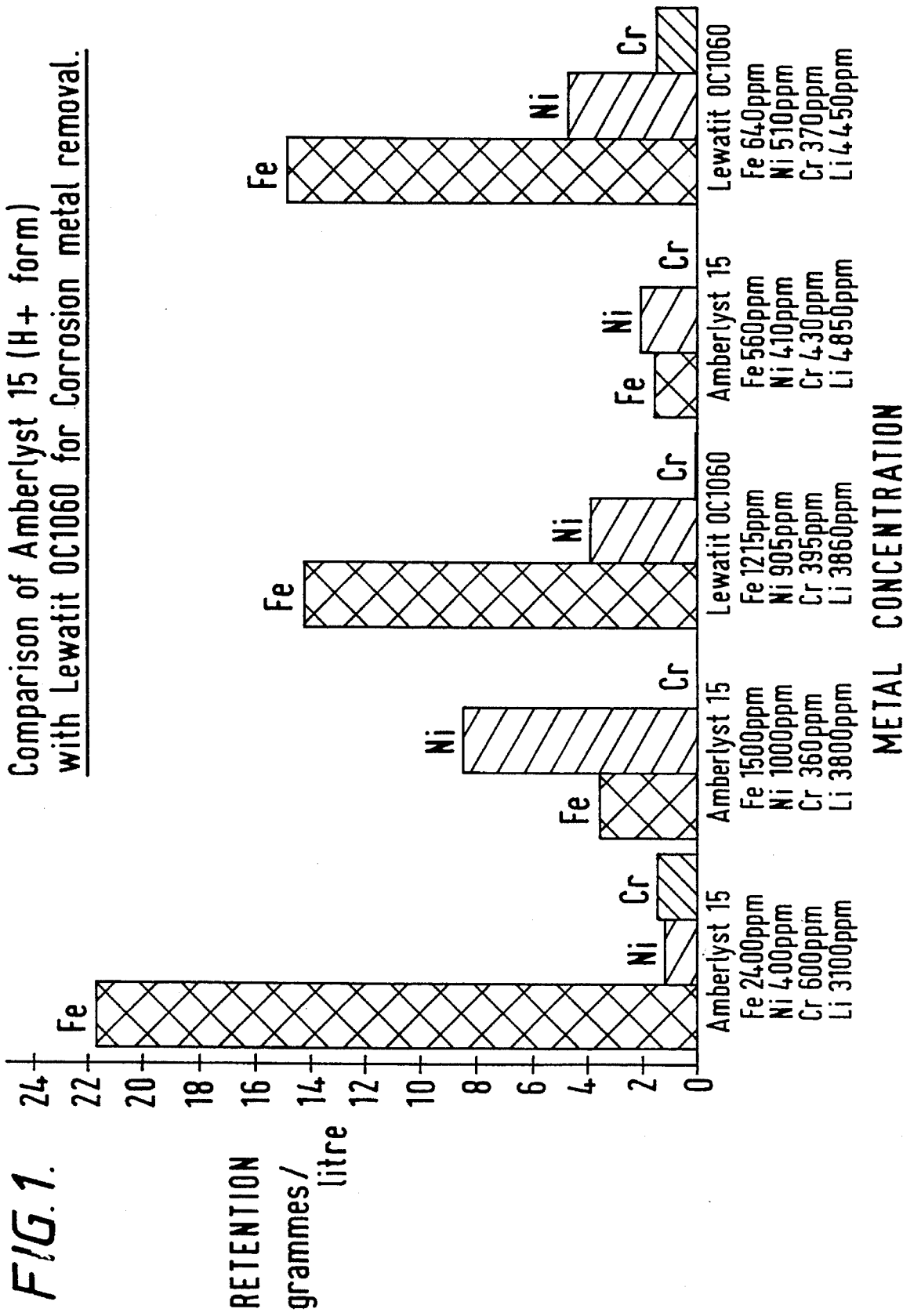

PROCESS FOR THE REMOVAL OF CORROSION METAL CONTAMINANTS FROM LIQUID COMPOSITIONS

This invention relates generally to the removal of corrosion metal contaminants from liquid compositions comprising carboxylic acids and/or anhydrides thereof and in particular to a process for the removal of corrosion metal contaminants from a liquid composition comprising a carboxylic acid and/or an anhydride thereof, a rhodium carbonylation catalyst, a carbonylation catalyst co-promoter and corrosion metal contaminants.

Processes for the production of carboxylic acids and anhydrides such as acetic acid and acetic anhydride by carbonylation are well known and are operated industrially.

Thus, UK patent GB 1,233,121 describes a process for the production of an organic acid or its corresponding ester by carbonylation using a rhodium catalyst. U.S. Pat. No. 4,374,070 describes preparation of acetic anhydride by carbonylation of methyl acetate in the presence of rhodium, an iodine compound and lithium. EP-A-087870 describes a process for the production of acetic anhydride with or without the net co-production of acetic acid.

In operating carbonylation processes over extended periods of time, corrosion metal contaminants such as compounds of iron, nickel, molybdenum, chromium and the like form and build up in the carbonylation reaction composition. Such corrosion metal contaminants, if present in sufficient amounts may have an adverse effect on the carbonylation reaction.

U.S. Pat. No. 4,628,041 describes a process for recovery of rhodium and iodine values in the manufacture of acetic acid by carbonylation by precipitating the rhodium to separate it from corrosion metal salts.

U.S. Pat. No. 4,007,130 describes a process for regenerating a spent carbonylation catalyst solution comprising a rhodium or iridium catalyst by contacting it with a cation exchange resin in its hydrogen form.

European patent application publication number EP-A-0384652 describes the behaviour of the Group IV B metals in increasing acetic acid productivity in liquid phase carbonylation in the presence of a rhodium catalyst and an iodide promoter. EP-A-0384652 proposes a process for treating process streams, arising in the manufacture of acetic acid from methanol, which process streams contain rhodium and typical corrosion metal salts characterised in that the process comprises selectively removing all the corrosion metals from the process stream with the exception of chromium, molybdenum or tungsten salts. According to EP-A-0384652 selective removal of, for example, iron from a process stream containing rhodium, iron, chromium, molybdenum and tungsten can be achieved by the use of selective ion exchange resins, electrodialysis, selective precipitation and the like. No details are given of suitable ion exchange resins.

European patent application publication number EP-A-0161874 describes rhodium-catalysed carbonylation of alcohols to produce carboxylic acids, for example methanol to acetic acid, in which iodide salts, preferably lithium iodide, are used as catalyst co-promoters. According to European patent application publication number EP-A-0265140 when regenerating catalyst solutions from the process described in EP-A-0161874 by the method described in U.S. Pat. No. 4,007,130 it is found that the lithium ion concentration is also reduced when the solution is passed through the cation exchange resin bed. The removal of the lithium ion from the catalyst solution greatly reduces the reactivity and stability of the reaction medium.

One method of overcoming this problem is described in European EP-A-0265140, which describes contacting a catalyst solution comprising rhodium, a finite concentration of lithium ions and corrosion metals with a cation exchange resin in its lithium form. According to EP-A-0265140 the cation exchange resins are either of the strong-acid or weak-acid type in their lithium form, preferably strong-acid type.

The use of lithium form cation exchange resin may reduce the loss of lithium from the solution. However, because lithium and corrosion metals compete for the same exchanger sites, as corrosion metals are taken up by the resin the effectiveness of the resin to remove further corrosion metals decreases as the relative concentrations of corrosion metals to lithium fall.

The removal of metallic corrosion products from carbonylation reactions which are carried out under anhydrous conditions is described in U.S. Pat. No. 5,124,290 which describes a process of (a) bringing a reaction solution containing the catalytic system and contaminated with metallic corrosion products, into contact with an ion exchanger; (b) separating the reaction solution; (c) desorbing the promoter before regeneration with acetic acid or acetic anhydride; (d) combining and recycling to the carbonylation reaction the eluate and solution from steps (c) and (b) respectively; (e) regenerating the ion exchanger obtained in step (c) with strong mineral acid and (f) washing with acetic acid or acetic anhydride. According to U.S. Pat. No. 5,124,290 it is preferred to use a strongly acid macroporous ion exchanger.

Strongly acid ion exchangers are not entirely satisfactory for the removal of corrosion metals from liquid compositions comprising carboxylic acids and/or anhydrides because they may char the acids and/or anhydrides.

The use of a chelating resin having an aminocarbon group and/or an iminocarbon group to remove metal ions from an organic compound or its solution is described in Japanese published application JO4022439. This publication does not consider the problem of selectively removing corrosion metal contaminants from a liquid composition which also comprises a rhodium carbonylation catalyst and a carbonylation catalyst co-promoter.

Therefore the technical problem to be solved is to provide an alternative process for the removal of corrosion metal contaminants from a liquid composition comprising a carboxylic acid and/or an anhydride thereof, a rhodium carbonylation catalyst, a carbonylation catalyst co-promoter and corrosion metal contaminants. Thus, according to the present invention there is provided a process for the removal of corrosion metal contaminants from a liquid composition comprising a carboxylic acid and/or an anhydride thereof, a rhodium carbonylation catalyst, a carbonylation catalyst co-promoter and corrosion metal contaminants which process comprises contacting the liquid composition with a chelating resin selective for the retention of corrosion metals and recovering a liquid composition having a reduced corrosion metal contaminant concentration.

The present invention solves the technical problems described above by the use of a chelating resin.

Chelating resins have functional groups which attach to a metal contaminant at more than one point. Chelating resins having bidentate and/or tridentate functional groups may be used. More than one chelating resin may be used, each of which may be selective for the removal of different corrosion metal contaminants.

The following chelating resins may be used in the process of the present invention:

(a) chelating resins having iminodiacetate functional groups, for example those having functional groups represented by the general formula (I):

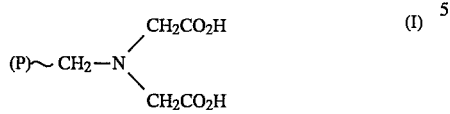

wherein (P) represents a polymer backbone. Suitable examples of this type of chelating resin include proton forms of Amberlite IRC-718, Lewatit TP207 and Lewatit TP208 (Trade Marks).

(b) chelating resins having aminophosphonic acid functional groups, for example those having functional groups represented by the general formula (II):

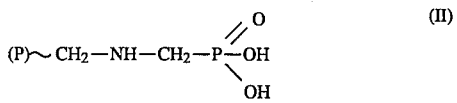

wherein (P) represents a polymer backbone. A suitable example of this type of chelating resin is proton form Bayer TP1060, previously called Lewatit VP OC 1060 MD, Purolite S940 and S950 and Duolite C467 (Trade Marks).

(c) chelating resins having functional groups represented by the general formula (III):

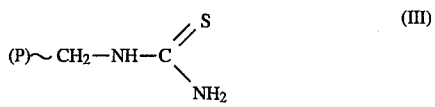

wherein (P) represents a polymer backbone. A suitable example of this type of chelating resin is Lewatit TP214 (Trade Mark).

(d) chelating resins having functional groups represented by the general formula (IV):

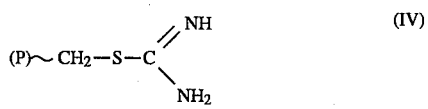

wherein (P) represents a polymer backbone. A suitable example of this type of chelating resin is Purolite S920 (Trade Mark).

(e) chelating resins having functional groups represented by the general formula (V):

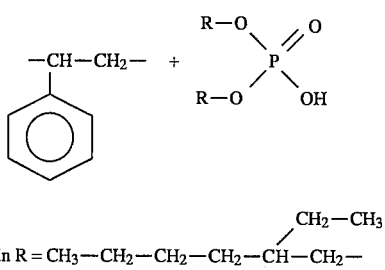

wherein R = $CH_3-CH_2-CH_2-CH_2-CH(CH_2-CH_3)-CH_2-$

A suitable example of this type of resin is Lewatit VP OC1026 (Trade Mark).

The chelating resin may be used in the proton form or in a metal exchanged form, for example sodium form. Preferably the resin is used in the proton form to avoid introducing metals into the liquid composition which may not be compatible with the carbonylation reaction.

The chelating resin may be based upon an organic backbone for example a polymer backbone such as polystyrene with optional cross-linking, for example with divinyl benzene or may be based upon an inorganic backbone, for example silica.

When polymer—backboned chelating resins are used they are preferably macroreticular resins. Gel resins which swell in the liquid composition may also be used.

Contacting the metal-contaminated liquid compositions with the chelating resin may be effected in a stirred vessel wherein the resin is stirred with the liquid composition with good agitation and the liquid composition having reduced corrosion metal contamination is then recovered by decantation, filtration, centrifuging etc. However, treatment of the liquid composition is usually effected by passing the metal-contaminated composition through a fixed-bed column of the resin. The treatment of the liquid composition may be carried out as a batch, semi-continuous or continuous operation either with manual or automatic control employing methods and techniques well known in the art of ion-exchange resins.

The liquid composition may be contacted with the chelating resin at any suitable temperature above the freezing point of the liquid composition and below the temperature at which the resin and/or composition exhibits unacceptable decomposition. The preferred temperature is in the range from about 20° C. to 70° C. If a temperature above the atmospheric boiling point of the liquid composition is used, operation at elevated pressure will be required to maintain the composition in a liquid state. However, pressure is not a critical variable. Generally, atmospheric pressure or a pressure slightly above atmospheric may be employed but superatmospheric or subatmospheric pressures may be used if desired.

The rate of flow of the liquid composition through a fixed-bed column of the resin during the corrosion metal removal process will, in general, be that recommended by the resin manufacturer and will usually be from about 1 to about 20 bed volumes per hour. Preferably, the flow rate is from about 1 to about 12 bed volumes per hour.

When the chelating resin has reached its capacity for corrosion metal contaminants it may firstly be rinsed with liquid compatible with carbonylation processes, for example carboxylic acid to remove residual liquid composition and then regenerated. The chelating resin may be regenerated by the methods recommended by the manufacturers to displace the retained corrosion metal contaminants. Suitably an aqueous solution of acetic acid and hydroiodic acid may be used to regenerate the chelating resins.

The process of the present invention may be operated as a batch or continuous process. Preferably more than one chelating resin bed is provided so that whilst liquid composition is being passed through one resin bed one or more other resin beds are being regenerated.

The process of the present invention is particularly applicable to the removal of corrosion metal contaminants such as iron, nickel, chromium, manganese and molybdenum, preferably iron and nickel. Each corrosion metal contaminant may be present in the liquid composition at up to its limit of solubility and typically this may be up to 10,000 ppm by weight metal. The amount of each corrosion metal removed from the liquid composition will depend upon the initial concentration, the capacity of the chelating resin, operating conditions and the like.

The carbonylation catalyst co-promoter may comprise an iodide of a quaternary amine, phosphine, arsenic or antimony compound or an iodide salt of an alkali or alkaline earth metal. Suitable quaternary phosphine carbonylation co-promoters are described in U.S. Pat. No. 4,333,884. Suitable quaternary amine carbonylation co-promoters are described in U.S. Pat. No. 4,333,884; U.S. Pat. No. 4,430,273 and EP-A-0479463.

The process of the present invention is particularly applicable to the removal of corrosion metal contaminants from liquid compositions in which the carbonylation catalyst co-promoters comprise one or more alkali metal iodides for example lithium, sodium and/or potassium iodide, particularly lithium iodide.

The liquid composition treated in the process of the present invention may also comprise unconverted carbonylation reactant, for example alcohols, ethers, halides and/or esters. Suitably the carbonylation reactant may comprise $C_1$ to $C_{10}$ alcohols for example methanol; dialkyl ethers wherein the alkyl groups independently have 1 to 10 carbon atoms, for example dimethylether; alkyl halides having 1 to 10 carbon atoms eg methyl iodide and esters of $C_1$ to $C_{10}$ alcohols with $C_2$ to $C_{11}$ carboxylic acids for example methyl acetate. The liquid composition treated in the process of the present invention may also comprise halogen-containing carbonylation promoters, for example alkyl halides such as methyl iodide. The liquid composition treated in the process of the present invention may also comprise a solvent compatible with the carbonylation process from which the liquid composition is derived and also compatible with the chelating resin. Where the liquid composition is derived from a carbonylation process for the production of carboxylic acids, the liquid composition may also comprise water.

The carboxylic acid and/or anhydride thereof may comprise a carboxylic acid having from 1 to 10 carbon atoms or anhydride thereof and is preferably acetic acid and/or acetic anhydride. The carboxylic acid or anhydride thereof may be the carbonylation product and/or solvent of the carbonylation process from which the liquid composition is derived.

Suitably, the liquid composition is derived from the liquid reaction composition of a liquid-phase carbonylation reaction for the production of carboxylic acids and/or anhydrides preferably acetic acid and/or acetic anhydride by the carbonylation of alcohols, ethers, esters and/or halides in the presence of a rhodium carbonylation catalyst, a halogen-containing carbonylation promoter and a carbonylation catalyst co-promoter. Suitable carbonylation reaction processes are described for example in GB 2146637-A, U.S. Pat. No. 4,994,608, U.S. Pat. No. 5,001,259, U.S. Pat. No. 5,026,908, EP-A-0144935 and EP-A-0144936 which relate to the production of carboxylic acids by carbonylation; in U.S. Pat. No. 5,003,104 which describes carbonylation processes for the production of carboxylic acids and carboxylic anhydrides; in U.S. Pat. No. 4,374,070 which describes preparation of acetic anhydride by carbonylation and in EP-A-87870 which describe the production of acetic anhydride with or without the net-coproduction of acetic acid.

Typically, carbonylation reaction processes operate at 150°–250° C. and at an elevated pressure with a partial pressure of carbon monoxide of 2–30 atmospheres.

The build up of corrosion metal contaminants in the liquid carbonylation reaction composition may be reduced by treating all or part of the carbonylation reaction composition. The liquid carbonylation reaction composition may be treated to remove some of the other components present in the composition prior to treatment in the process of the present invention. In a typical liquid phase carbonylation process to which the process of the present invention is applicable, liquid carbonylation reaction composition is withdrawn from a carbonylation reactor and passed to a flash zone at a pressure below that of the reactor wherein with or without the addition of heat, a vapour fraction comprising volatile components such as unreacted carbonylation reactant, halogen-containing carbonylation promoter and carbonylation product is separated from a liquid fraction comprising involatile components such as rhodium carbonylation catalyst; and carbonylation catalyst co-promoter, for example an iodide of a quaternary amine, phosphine, arsenic or antimony compound or an alkali or alkaline earth metal iodide. The carbonylation product is recovered from the vapour fraction by, for example distillation, the remaining components being recycled to the carbonylation reactor. The liquid fraction from the flash zone is recycled to the carbonylation reactor. It has been found that corrosion metal contaminants can be present in any of the process streams. However, their removal from the flash zone liquid fraction by conventional processes can be difficult because of the presence of rhodium carbonylation catalyst and carbonylation catalyst co-promoter. By treating at least a part of this liquid fraction by the process according to the present invention, the build up of corrosion metal contaminants in the liquid carbonylation reaction composition can be reduced. Preferably, a slipstream is removed from the flash zone liquid fraction and treated according to the process of the present invention to remove corrosion metal contaminants and provide a liquid composition having reduced corrosion metal contaminants which is recycled to the carbonylation reactor.

In an alternative embodiment the process of the present invention may be used to remove corrosion metals from process streams comprising acetic acid and/or acetic anhydride such as are to be found in the processes for recovering rhodium catalyst values from tar-containing process streams derived from the production of acetic anhydride. Examples of such processes are described in EP-A-0087870, EP-A-0255389, EP-A-0314352 and EP-A-0584964.

BRIEF DESCRIPTION OF DRAWING

The process of the present invention will now be illustrated by reference to the following Examples and FIG. 1. FIG. 1 represents in block diagram form, the results of corrosion metal capacity determinations for Amberlyst 15 and Lewatit OC1060 resins:

EXAMPLES 1–3 AND EXPERIMENT A

A liquid composition from a carbonylation process for the production of acetic anhydride and comprising by weight acetic acid (31.6%), acetic anhydride (13%), n-methyl imidazolium iodide (estimated about 30%), methyl acetate (6.7%), methyl iodide (4.4%), iron (3880 ppm), nickel (2180 ppm), chromium (1330 ppm), manganese (345 ppm), molybdenum (630 ppm) and rhodium (617 ppm) was treated to remove corrosion metals. In each experiment 100 ml of resin was prewashed with acetic acid (500 ml) and packed into a fixed bed column. The liquid composition was passed through the resin at ambient temperature and pressure at a liquid hourly space velocity of 2 and the liquid effluent composition having reduced corrosion metal contaminant concentration was analysed to determine the retention of the corrosion metal contaminants.

For Examples 1 to 3 chelating resins IRC-718, TP207 and OC1060 were used. In Experiment A which is not according to the present invention, a strong acid resin Amberlyst 15 was used. The resins were used in the proton form. The results are shown in Table 1 below:

TABLE 1

| | Example | | | Experiment |
|---|---|---|---|---|
| | 1 | 2 | 3 | A |
| Resin | IRC-718 | TP207 | OC1060 | Amberlyst 15 |
| Metal removal % | | | | |
| Iron | 70.2 | 22.2 | 33.9 | 0 |
| Nickel | 86.4 | 53.7 | 33.0 | 5.0 |
| Chromium | 38.5 | 14.0 | 16.5 | 0 |
| Manganese | 69.6 | 29.6 | 55.4 | 0.7 |
| Molybdenum | 0 | 6.7 | 18.6 | 28 |
| Rhodium | 4.9 | 0 | 0 | 11 |

The results in Table 1 show that in these experiments, the chelating resins of the present invention were superior to a strong acid resin such as Amberlyst 15 for corrosion metal contaminant removal.

EXPERIMENT B

These experiments, which are not according to the present invention, illustrate a problem associated with a strong acid resin when trying to remove corrosion metals to very low levels in the presence of lithium iodide carbonylation catalyst co-promoter.

A liquid composition was prepared to have the following composition by weight:

| | |
|---|---|
| Water | 10% |
| Methyl acetate | 0.7% |
| Acetic Acid | 72% |
| Methyl Iodide | 2% |
| Iron | 2400 ppm |
| Nickel | 400 ppm |
| Chromium | 600 ppm |
| Lithium | 3100 ppm |

The metals were added as the iodides.

This liquid composition was passed through a 60 ml fixed-bed column of strong acid Amerblyst 15 resin for a period of 60 hours at a liquid hourly space velocity of 4 and at ambient temperature. The resin was used as supplied in the proton form and was conditioned by soaking in acetic acid prior to use. The liquid composition having reduced corrosion metal contamination passing out of the resin bed was recycled to the feed point of the resin bed. The liquid feed composition was analysed at intervals to determine the residual concentration of metals and from this the retention of metals by the resin bed was calculated. The resin removed a very small amount of lithium but the values were difficult to estimate. The uptakes of corrosion metals were iron 21.7 grams/liter, nickel 1.2 g/l and chromium 1.5 g/l expressed as weight of metal per liter of soaked resin.

The experiment was repeated with a similar liquid composition except that the metal concentrations were as follows: iron 1500 ppm, nickel 1000 ppm, chromium 360 ppm and lithium 3800 ppm. The uptakes of corrosion metals were iron 3.6 g/liter, nickel 8.5 g/l and chromium 0 g/l.

The experiment was repeated with a similar liquid composition except that the metal concentrations were as follows: iron 560 ppm, nickel 410 ppm, chromium 430 ppm and lithium 4850 ppm. The uptakes of corrision metals were iron 1.6 g/liter, nickel 2.1 g/l and chromium 0 g/l.

The results are shown in block graph form in FIG. 1. As can be seen the capacity of Amberlyst 15 for corrosion metals is strongly affected by the concentration of corrosion metals relative to lithium concentrations. The resin is ineffective when the concentration of corrosion metal contaminants is low relative to the concentration of lithium.

EXAMPLE 4

To illustrate the benefit associated with using a chelating resin, comparative Experiment B was repeated using Lewatit OC1060 (capacity 2.9 meq/ml water wet proton form). A similar liquid composition to Experiment B was used except that the metal concentrations were as follows: iron 1215 ppm, nickel 905 ppm, chromium 395 ppm and lithium 3860 ppm. The uptake of corrosion metals were iron 14.2 g/liter, nickel 3.9 g/l and chromium 0.1 g/l.

The Example was repeated with a similar liquid composition except that the metal concentrations were as follows: iron 640 ppm, nickel 510 ppm, chromium 370 ppm and lithium 4450 ppm. The uptake of corrosion metals were iron 14.8 g/liter, nickel 4.7 g/l and chromium 1.5 g/l.

The results are shown in block graph form in FIG. 1 with the data from Experiment B included for comparison. From the experiments it can be seen that the retention of corrosion metal contaminants by the chelating resin is unaffected, within experimental error, by the concentration ratios of corrosion metals to lithium.

EXAMPLE 5

This Example shows the effectiveness of Lewatit OC1060 over a wide range of lithium salt carbonylation co-promoter concentrations. Solutions with similar compositions to that in Experiment B were prepared containing the following metal concentrations: iron 600 ppm, nickel 450 ppm and chromium 365 ppm. The lithium concentrations were varied between 0 and 9000 ppm. On repeating the experimental procedure of Experiment B the retention of metals by the resin is given in Table 2.

TABLE 2

The effect of Lithium concentration on Lewatit OC1060 Performance

| Lithium conc. (ppm) | Iron Retention (g/l) | Nickel Retention (g/l) | Chromium Retention (g/l) |
|---|---|---|---|
| 0 | 11.0 | 3.0 | 1.3 |
| 3700 | 13.9 | 2.0 | 1.3 |
| 4200 | 11.9 | 2.0 | 1.0 |
| 9000 | 14.0 | 1.5 | 0.5 |

EXAMPLE 6

To illustrate the benefit associated with using a chelating resin, the experiments in example 4 were repeated using Amberlite IRC718 (capacity 1.1 meq/ml water wet proton form). A similar liquid composition was used except that the metal concentrations were as follows: iron 1500 ppm, nickel 1100 ppm, chromium 520 ppm and lithium 4850 ppm. The retention of corrosion metals by the resin was iron 5.4 g/liter, nickel 18.5 g/l and chromium 1.8 g/l.

The experiment was repeated with a similar liquid composition except that the metal concentrations were as follows: iron 660 ppm, nickel 450 ppm, chromium 145 ppm and lithium 4990 ppm. The retention of corrosion metals by the resin was iron 4.9 g/liter, nickel 9.9 g/l and chromium 1.0 g/l.

Thus it can be seen that different corrosion metals may be selectively removed by choice of the particular chelating resin used.

EXAMPLE 7

To illustrate the effect on rhodium present in the solution, a 1 liter sample from the flash separation zone of a typical carbonylation process for the carbonylation of methanol to produce acetic acid was taken. This contained the following: lithium iodide 14 wt %, iron 305 ppm, nickel <10 ppm, chromium 60 ppm and rhodium 640 ppm. The solution was placed in contact with 50 g of Lewatit OC1060 for 48 hours at ambient temperature and pressure. An analysis of the solution after treating with the resin showed that it contained the following: iron 55 ppm, nickel <10 ppm, chromium 60 ppm and rhodium 630 ppm.

This shows that the resin is able to remove corrosion metals to very low levels in the presence of high levels of lithium iodide carbonylation catalyst co-promoter and rhodium carbonylation catalyst.

EXPERIMENT C

To illustrate the inability of strong acid Amberlyst 15 resin to reduce the concentration of corrosion metals in solution to low levels in the presence of lithium iodide carbonylation catalyst co-promoter there was used a 1.5 liter sample of a typical carbonylation liquid composition for the carbonylation of methanol to acetic acid, containing the following: lithium iodide 10 wt %, iron 2240 ppm, nickel <10 ppm, chromium 23 ppm, and rhodium 360 ppm. The aggregate of these metals was calculated to be significantly less than the expected total capacity of the resin (approx. 1.7 meq/ml water wet proton form resin). The solution was passed several times through two 800 ml beds of lithium-exchanged Amberlyst 15 at a liquid hourly space velocity of 0.25. An analysis of the solution after treatment showed that it still contained the following: iron 900 ppm, nickel <10 ppm, chromium 35 ppm, rhodium 355 ppm.

This experiment shows that although the strong acid resin has a high capacity in terms of available sites it is unable to selectively remove the iron to low concentrations in the presence of lithium iodide. This is not an example according to the present invention.

EXAMPLE 8

To illustrate a benefit associated with using a chelating resin at elevated temperature, Example 4 was repeated using Lewatit OC1060 at 40° C. A similar liquid composition was used except that the metal concentrations were as follows: iron 765 ppm, nickel 315 ppm, chromium 425 ppm and lithium 4560 ppm. The retention of corrosion metals was iron 20.2 g/liter, nickel 3.0 g/l and chromium 3.6 g/l.

The experiment was repeated with metal concentrations as follows: iron 860 ppm, nickel 470 ppm, chromium 410 ppm and lithium 5062 ppm. The retention of corrosion metals was iron 17.0 g/liter, nickel 2.7 g/l and chromium 1.2 g/l.

From these experiments it can be seen that the selectivity of the resin towards iron has increased compared to experiments at ambient conditions.

We claim:

1. A process for the removal of corrosion metal contaminants from a liquid composition comprising a carboxylic acid, an anhydride thereof or a mixture thereof, a rhodium carbonylation catalyst, a carbonylation catalyst co-promoter and corrosion metal contaminants which process comprises contacting the liquid composition with a chelating resin selective for the retention of corrosion metals and recovering a liquid composition having a reduced corrosion metal contaminant concentration, wherein said chelating resin is selected from the group consisting of chelating resins having:

(a) iminodiacetate functional groups;
(b) aminophosphonic acid functional groups;
(c) functional groups represented by the general formula

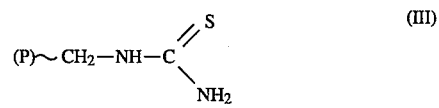

wherein (P) represents a polymer backbone;

(d) functional groups represented by the general formula:

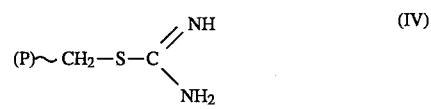

wherein (P) represents a polymer backbone; and (e) functional groups represented by the general formula:

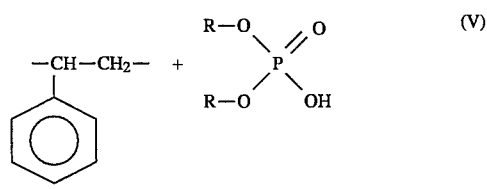

wherein

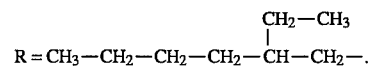

2. A process as claimed in claim 1 in which the iminodiacetate functional groups are represented by the general formula:

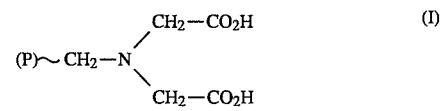

wherein (P) represents a polymer backbone.

3. A process as claimed in claim 1 in which the aminophosphonic acid functional groups are represented by the general formula:

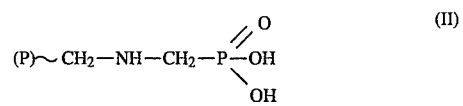

wherein (P) represents a polymer backbone.

4. A process as claimed in any one of claims 1 to 3 in which the chelating resin is in the proton form.

5. A process as claimed in claim 4 in which the liquid reaction composition comprises acetic acid, acetic anhydride or a mixture thereof.

6. A process as claimed in claim 5 in which the corrosion metal contaminants are selected from the group consisting of iron, nickel, chromium, manganese and molybdenum.

7. A process as claimed in claim 6 in which the carbonylation catalyst co-promoter is selected from the group consisting of iodides of quaternary amine, phosphine, arsenic and antimony compounds.

8. A process as claimed in claim 6 in which the carbonylation catalyst co-promoter is an iodide salt of an alkali metal.

9. A process as claimed in claim 8 in which the carbonylation catalyst co-promoter is lithium iodide.

10. A process for the production of carboxylic acids, carboxylic acid anhydrides or mixtures thereof by the liquid-phase carbonylation reaction of a reactant selected from the group consisting of alcohols, ethers, esters and halides in the presence of a rhodium carbonylation catalyst, a halogen-containing carbonylation promoter and a carbonylation catalyst co-promoter in which a liquid composition derived from the carbonylation reaction and comprising carboxylic acid, carboxylic acid anhydride or a mixture thereof, rhodium carbonylation catalyst, carbonylation catalyst co-promoter and corrosion metal contaminants is contacted with a chelating resin selective for the retention of corrosion metals and a liquid composition have a reduced corrosion metal contaminant concentration is recovered therefrom and recycled to the carbonylation reaction wherein said chelating resin is a resin as defined in claim 9

11. A process as defined in claim 1 wherein the chelating resin has iminodiacetate functional groups.

12. A process as defined in claim 1 wherein the chelating resin has functional groups represented by the general formula:

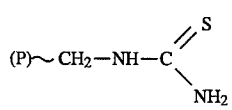  (III)

13. A process as defined in claim 1 wherein the chelating agent has functional groups represented by the general formula:

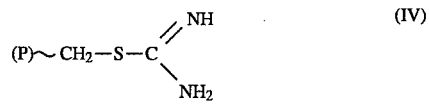  (IV)

where P represents a polymer backbone.

14. A process as defined in claim 1 wherein the chelating agent has functional groups represented by the general formula:

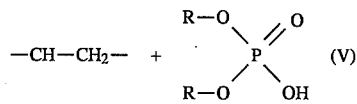  (V)

15. A process as defined in claim 10, wherein the chelating resin is a resin defined in claim 3.

16. A process as defined in claim 10, wherein the chelating resin is a resin defined in claim 4.

17. A process as defined in claim 10, wherein the chelating resin is a resin defined in claim 13.

18. A process as defined in claim 10 wherein the chelating resin is a resin defined claim 14.

19. A process as defined in claim 10 wherein the chelating resin is a resin defined claim 15.

20. A process as defined in claim 10 wherein the chelating resin is a resin defined in claim 14.

* * * * *

UNITED STATES PATENT AND TRADEMARK OFFICE
CERTIFICATE OF CORRECTION

PATENT NO. : 5,466,876

DATED : November 14, 1995

INVENTOR(S) : ANDREW R. McCLARRON, STEPHEN J. SMITH, DERRICK J. WATSON, BRUCE L. WILLIAMS and EUAN S. ROSS It is certified that error appears in the above-indentified patent and that said Letters Patent is hereby corrected as shown below:

Col. 12, line 31:
Claim 18,      after "defined" and before "claim" insert
       --in--.
Col. 12, line 33:
Claim 19,      after "defined" and before "claim" insert
       --in--.

Signed and Sealed this

Second Day of April, 1996

Attest:

BRUCE LEHMAN

Attesting Officer

Commissioner of Patents and Trademarks